United States Patent [19]

Ambrosius et al.

[11] Patent Number: 5,759,257

[45] Date of Patent: Jun. 2, 1998

[54] COLOR PIGMENTS

[75] Inventors: Klaus Ambrosius, Doeburg; Matthias Schraml-Marth, Zwingenberg, both of Germany

[73] Assignee: Merck Patent Gesellschaft mit Beschrankter Haftung, Germany

[21] Appl. No.: 644,858

[22] Filed: May 10, 1996

[30] Foreign Application Priority Data

May 12, 1995 [DE] Germany .................. 195 16 960.3

[51] Int. Cl.$^6$ .................................................. C09C 1/22
[52] U.S. Cl. ..................... 106/450; 106/415; 106/417; 106/418; 106/457; 106/459
[58] Field of Search ................................ 106/415, 417, 106/418, 450, 456, 457, 459, 481

[56] References Cited

U.S. PATENT DOCUMENTS

| | | | |
|---|---|---|---|
| 4,867,793 | 9/1989 | Franz et al. | 106/415 |
| 4,867,795 | 9/1989 | Ostertag et al. | 106/415 |
| 5,106,419 | 4/1992 | Hechler et al. | 106/459 |
| 5,273,576 | 12/1993 | Sullivan et al. | 106/418 |
| 5,354,374 | 10/1994 | Prengel | 106/450 |

*Primary Examiner*—Michael Marcheschi
*Attorney, Agent, or Firm*—Millen, White, Zelano & Branigan, P.C.

[57] ABSTRACT

The present invention relates to color pigments based on substrates which are coated with a doped layer of iron(III) oxide, to processes for their preparation and to their use, especially in aqueous coating systems.

17 Claims, No Drawings

COLOR PIGMENTS

The present invention relates to color pigments based on substrates coated with a doped layer of iron(III) oxide, to processes for their preparation and to their use, especially in aqueous coating systems.

BACKGROUND OF THE INVENTION

Pigments containing iron oxide have been described on numerous occasions in the literature. Pearl luster pigments whose gold hue is intensified by the addition of iron oxides are known from DE 14 67 468. A specific process for the preparation of a luster pigment with added iron oxide is described in German application P 19 59 998. Here, in addition, the layer containing iron oxide is also coated with a layer of titanium dioxide and/or zirconium dioxide. The iron(III) oxide present in these luster pigments is precipitated in the acid range from iron(III) salt solutions. DE 22 44 298 discloses gold-colored pigments based on flakes of mica coated with titanium dioxide and aftercoated with an $Fe_2O_3$ layer prepared by oxidation of iron(II) hydroxide. SU 16 999 930 A1 discloses red pigments with an increased mother-of-pearl luster, based on mica platelets coated with $Fe_2O_3$ and $B_2O_3$.

DE 41 35 742 A1 describes $B_2O_3$-doped iron oxide pigments whose surface is particularly smooth. The magnetite pigments, prepared by the nitro-benzene process, can be subsequently annealed in air and thus converted to red pigments with various shades of color. U.S. Pat. No. 5,273,576 discloses pearl luster pigments in which mica is covered with an $SnO_2$—, ZnO— or $ZrO_2$-doped iron(III) oxide layer, a feature of which pigments is their enhanced chroma.

The iron oxide pigments known from the prior art are notable for their high color value and their weather resistance when used in non-aqueous coating systems. In aqueous coating systems, however, which are becoming increasingly important, especially in the automotive industry, the known iron oxide pigments all exhibit the disadvantage that they lead to the formation of microfine blisters within the coating film. These blisters cause an increase in the scattering of light and therefore have an adverse effect on the color and gloss of the pigmented aqueous coating system.

A further disadvantage is the reduction in the distinctness of image (DOI) and the impairment of the regeneration capacity of the pigmented coating.

SUMMARY OF THE INVENTION

An object of the present invention, therefore, was to find modified pigments containing iron oxide which can be readily dispersed in aqueous coating systems without losing their properties and which have none of the above-mentioned disadvantages.

Upon further study of the specification and appended claims, further objects and advantages of this invention will become apparent to those skilled in the art.

It has surprisingly now been found that substrates coated with an $SiO_2$— and $ZrO_2$-doped iron(III) oxide layer are notable for their high color value and their luster and can be incorporated without problems into aqueous coating systems.

The invention therefore provides color pigments based on substrates coated with iron(III) oxides, characterized in that the iron oxide layer is doped with $ZrO_2$ and $SiO_2$.

The invention additionally provides a process for the preparation of the pigments according to the invention, which is distinguished in that an aqueous iron(III) salt solution, zirconium salt solution and a water-soluble silicon compound are added simultaneously or in succession to the aqueous substrate suspension under conditions which lead to the deposition of the corresponding iron, zirconium and silicon hydroxides or oxides, and the pigment is then separated off, washed, dried and calcined at temperatures >500° C.

Suitable base substrates for the coating are both opaque and transparent platelet-shaped or nonplatelet-shaped substrates. Preferred substrates are phyllosilicates and also platelet-shaped materials coated with metal oxides. Particularly suitable substrates are mica, talc, kaolin, bismuth oxychloride, flakes of glass, of $SiO_2$ or of ceramics, synthetic carrier-free platelets or other comparable materials. Also suitable, in addition, are metal flakes, for example aluminum flakes, or platelet-shaped metal oxides, for example platelet-shaped iron oxide, and micas coated with colored or colorless metal oxides such as $TiO_2$, $Fe_2O_3$, $SnO_2$, $Cr_2O_3$, ZnO and other metal oxides, alone or mixed in a single layer or in successive layers. These pigments, known as pearl luster pigments, are known for example from the German patents and patent applications 14 67 468, 19 59 998, 20 09 566, 22 14 545, 22 15 191, 22 44 298, 23 13 331, 25 22 572, 31 37 808, 31 37 809, 31 51 343, 31 51 354, 31 51 355, 32 11 602 and 32 35 017.

The platelet-shaped substrates generally have a thickness of from about 0.1 to 5 μm and, in particular, of from 0.2 to 4.5 μm. The extent in the two other dimensions is customarily from about 1 to 250 μm, in particular from 2 to 200 μm.

The pigments according to the invention are prepared by first preparing an aqueous suspension of the substrate. An aqueous iron(III) salt solution, an aqueous zirconium salt solution and an aqueous silicate solution are metered simultaneously or, preferably, in succession into the suspension, the pH of the reaction mixture being maintained by simultaneous addition of an acid or base in a range which brings about hydrolysis of the metal salt. Under these conditions, the $Fe_2O_3$ and $ZrO_2$ and $SiO_2$ or the corresponding hydroxides are precipitated onto the substrate surface either successively or simultaneously. The temperature of the reaction solution is not very critical and is usually from about 20°–80° C. The oxides or hydroxides are generally precipitated at a pH of from about 3 to 12. By the addition of acids, preferably mineral acids such as, for example, HCl, $HNO_3$, $H_2SO_4$, and bases such as, for example, NaOH, KOH, $Na_2CO_3$, $K_2CO_3$, $NH_3$, the pH is easily maintained at a constant level.

After the separation, washing and drying of the coated substrates, the pigments are calcined at temperatures >500° C., preferably at 800°–850° C. The calcining time depends in general on the thickness of the precipitated layer; it can be from a few minutes to several hours, but preferably from about 20 to 120 minutes.

As metal salts from which the hydroxides or oxides can be precipitated it is possible to use all water-soluble salts which can be hydrolyzed by bases or acids.

Particularly suitable iron(III) salts are the halides, nitrates and sulfates, preferably iron(III) chloride.

The zirconium compounds are preferably employed in the form of the chloride $ZrCl_4$ or basic chloride $ZrOCl_2$.

The silicon dioxide is added to the suspension in the form of a water-soluble inorganic silicon compound. Suitable preparations are the aqueous solutions of alkali metal silicates which are available commercially under the name "waterglass," for example potassium waterglass and sodium waterglass.

All conceivable ratios of $ZrO_2$ to $SiO_2$ can be used when doping the iron(III) oxide layer. A positive effect on color strength and luster is observed in particular when the ratio of $ZrO_2$ to $SiO_2$ is from about 10:1 to 0.1:1, preferably from 5:1 to 0.5:1. The amount of dopant, i.e., the sum of $ZrO_2$ and $SiO_2$, in the iron(III) oxide layer is from 0.1 to 10% by weight, preferably from 0.1 to 5% by weight, in particular from 0.1 to 3% by weight.

The amount of doped iron(III) oxide layer on the substrate is preferably about 25–70 wt %, particulary 30–50 wt %, based on the total weight of the pigment.

The color pigments prepared by the process according to the invention are notable for their high color strength, luster and opacity. They are compatible with a wide range of colored systems, preferably from the area of varnishes, paints and printing inks.

Because of their high light stability and weather resistance they are outstandingly suitable for automotive finishes, especially those based on aqueous systems.

Consequently, the invention also provides for the use of the iron oxide pigments according to the invention in formulations such as paints, varnishes, printing inks, plastics and cosmetic preparations.

The pigments are generally employed in the formulation in amounts of up to 30% at most, preferably from 0.5 to 10%.

The invention additionally provides formulations comprising the pigments according to the invention.

The examples given below are intended to illustrate the invention without limiting it.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application P 95 16 960.3, are hereby incorporated by reference.

EXAMPLES

Example 1

A suspension of 10 kg of mica with a particle size of 10–50 μm in 150 l of water is heated to 75° C. with stirring. The pH is adjusted to 3 using 5% HCl. Then an aqueous $FeCl_3$ solution (Fe content 3% by weight) is added, the pH being maintained at 3.0 using about 30% NaOH. When the red interference color has been obtained, the addition of the $FeCl_3$ solution is discontinued and the mixture is stirred for a further 15 minutes.

After adjusting the pH to 3.2 with 5% NaOH, a solution is added, consisting of 175 g of $ZrOCl_2 \times 8\ H_2O$ in 15 l of water, over the course of one hour. Stirring is continued for 15 minutes and the pH is adjusted to 9 with 5% NaOH. Over the course of one hour an aqueous solution of sodium silicate [180 ml of sodium silicate (27% by weight) in 15 l of water] is metered in, the pH being held constant with 5% HCl. After the end of the addition, the pH is adjusted to 6.5 with 5% HCl and the suspension is stirred for a further 15 minutes. The product is filtered off, washed with water, dried and calcined at 850° C.

Example 2

Comparison Example

A suspension of 10 kg of mica with a particle size of 10–50 μm in 150 l of water is heated to 75° C. with stirring. The pH is adjusted to 3.0 using 5% HCl. Then an aqueous $FeCl_3$ solution (Fe content 3% by weight) is added, the pH being held constant by simultaneous addition of 30% NaOH. When the red interference color has been obtained, the addition of the $FeCl_3$ solution is discontinued and the mixture is stirred for a further 15 minutes.

The pH is adjusted to 5.0 using 5% NaOH and this suspension is stirred for a further 15 minutes. The product is filtered off, washed with water, dried and calcined at 850° C.

The pigments are assessed using the condensed water test.

The pigments from Example 1 and the comparison example are incorporated into a commercial aqueous varnish and the test specimens are prepared by spraying the resulting paints onto a metal panel.

Testing is in accordance with DIN 50017 (condensed water test—constant climatic conditions).

Test duration: 240 h at 40° C.

The assessment of the swelling process is carried out visually in accordance with DIN 53230. In the rating scale, 0 denotes "unchanged" and 5 denotes "severely altered."

The degree of blistering is assessed visually in accordance with DIN 53209. m denotes the frequency of occurrence of the blisters per unit area while g denotes the size of the blisters. The rating scale ranges from 0 (very good) to 5 (very poor).

The gloss is assessed using a reflectometer in accordance with DIN 67530.

The distinctness of image (DOI) is determined in accordance with ASTM EU 30-91.

The test results are given in Table 1:

TABLE 1

| Example | Swelling | Blistering | Crosshatch Test | Assessment of Gloss at 20° in % | Distinctness of Image in % |
|---|---|---|---|---|---|
| 1 | 1–2 | m 0/g 0 | Gt 0 | 94 | 97 |
| 2 | 4 | m 3–4/g 0–1 | Gt 0 | 90 | 59 |
| Blank sample (without pigment) | 1 | m 0/g 0 | Gt 1 | 97 | 94 |

The pH is adjusted to 3 using 5% HCl. Then an aqueous $FeCl_3$ solution (Fe content 3% by weight) is added, the pH Table 1 shows that the pigment according to the invention suppresses the formation of fine microblisters in the aqueous paint, increases the distinctness of image and has much less of an effect on the gloss than the untreated pigment.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A color pigment comprising a platelet-shaped substrate with an iron(III) oxide coating, wherein the iron(III) oxide coating is doped with zirconium dioxide and silicon dioxide.

2. A color pigment according to claim 1, wherein the proportion of the sum of zirconium dioxide and silicon dioxide in the iron(III) oxide coating is from 0.1 to 10% by weight.

3. A color pigment according to claim 1, having a ratio of $ZrO_2$ to $SiO_2$ of from 10:1 to 0.1:1.

4. A color pigment according to claim 2, having a ratio of $ZrO_2$ to $SiO_2$ of from 10:1 to 0.1:1.

5. A color pigment according to claim 1, wherein the platelet-shaped substrate comprises mica platelets, silica flakes, glass flakes or ceramic flakes.

6. A process for the preparation of a color pigment according to claim 1, comprising adding an aqueous iron (III) salt solution, a zirconium salt solution and a water-soluble silicon compound to an aqueous suspension of the substrate under conditions such that corresponding oxides or hydroxides are deposited on the substrate, separating, washing, drying and calcining the coated substrate at a temperature >500° C.

7. A paint, colorant, plastic or cosmetic composition comprising a color pigment according to claim 1 and a conventional auxiliary for said paint, colorant, plastic or cosmetic composition.

8. An aqueous coating system composition comprising a color pigment according to claim 1.

9. The aqueous coating system of claim 8, wherein the color pigment is dispersed in the system.

10. The color pigment of claim 1, wherein the substrate has a thickness of from about 0.1 to 5 µm and a size of about 1 to 250 µm in the other two dimensions.

11. The color pigment of claim 1, wherein the proportion of the sum of zirconium dioxide and silicon dioxide present in the iron(III) oxide coating is from 0.1 to 5% by weight.

12. The color pigment of claim 1, wherein the proportion of the sum of zirconium dioxide and silicon dioxide present in the iron(III) oxide coating is from 0.1 to 3% by weight.

13. The color pigment of claim 1, wherein the amount of doped iron(III) oxide coating on the substrate is about 25–70% by weight based on the total weight of the pigment.

14. The color pigment of claim 1, wherein the amount of doped iron(III) oxide coating on the substrate is 30–50% by weight based on the total weight of the pigment.

15. The process of claim 6, wherein the corresponding oxides or hydroxides are deposited on the substrate at a temperature of 20°–80° C. and a pH of 3–12.

16. The process of claim 6, wherein the iron(III) salt is iron(III) chloride, the zirconium salt is $ZrCl_4$ or $ZrOCl_2$ and the water-soluble silicon compound is a waterglass.

17. The color pigment of claim 1, wherein the substrate is mica, mica coated with at least one metal oxide layer, glass flakes, silica flakes, ceramic flakes, metal flakes or platelet-shaped metal oxide.

* * * * *